| United States Patent [19] | [11] Patent Number: 4,985,436 |
| Pettit | [45] Date of Patent: Jan. 15, 1991 |

[54] COMPOSITION OF MATTER FOR INHIBITING LEUKEMIAS AND SARCOMAS

[75] Inventor: George R. Pettit, Paradise Valley, Ariz.

[73] Assignee: Arizona Board of Regents, Tempe, Ariz.

[21] Appl. No.: 581,188

[22] Filed: Feb. 17, 1984

[51] Int. Cl.$^5$ .............................................. A61K 31/47
[52] U.S. Cl. .................................... 514/287; 514/256; 546/65; 544/296
[58] Field of Search ......................... 546/65; 424/256; 514/287, 256; 544/333, 296

[56] References Cited

U.S. PATENT DOCUMENTS 3,583,993  6/1971  Okamoto et al. ...................... 546/65

OTHER PUBLICATIONS

Ohta et al., Tetrahedron Letters, No. 27, (1975), pp. 2279–2282.

Primary Examiner—Donald G. Daus
Attorney, Agent, or Firm—Richard R. Mybeck

[57] ABSTRACT

A new antineoplastic substance denominated "pancratistatin". Methods of isolating natural and synthetic pancratistatin and 7-deoxynarciclasine and the pharmaceutically acceptable derivatives thereof to make a pharmaceutical preparation therefrom and methods for treating a host afflicted with a neoplasm with said preparations.

10 Claims, No Drawings

COMPOSITION OF MATTER FOR INHIBITING LEUKEMIAS AND SARCOMAS

INTRODUCTION

The present invention relates generally to a new antineoplastic substance denominated "pancratistatin", its synthetic counterpart and pharmaceutically acceptable derivatives thereof. The invention further comprises methods for obtaining pancratistatin and 7-deoxynarciclasine, proceedures for creating a pharmacutical preparation therefrom, and methods for treating a host, afflicted with a neoplastic growth, therewith.

BACKGROUND OF INVENTION

As early as the fourth century BC, attention was directed to certain medical and/or poisonous plant species. To determine the presence of alkaloid constituents in such species, see: Gibbs, R.D. "Chemotaxonomy of Flowering Plants" Vol III, McGills-Queens University Press. Montreal, 1974, p 1924. Over time, more than thirty species of the relatively large Amaryllidaceae family found use in the primitive treatment of cancer (See: Hartwell, J. L. *Loydia*, 1967, 30, 391).

In the continuing effort to locate and define various natural and synthesizable substances for treatment of one or more varieties of cancer, research chemists continue to look at natural flora and fauna in an attempt to isolate and identify substances which exhibit antineoplastic activity while substantially minimizing, if not totally eliminating, some of the severe side effects accompanying known chemotherapeutic agents.

It is in the further pursuit of these goals that plant species heretofore ignored are now being examined to determine whether they contain constituents which when isolated will exhibit antineoplastic activity.

Accordingly, a principal object of the present invention is to provide new agents useful in the retardation or remission of one or more types of cancer.

Another object of the present invention is to provide methods and procedures for isolating antineoplastic substances from plant life in a form whereby they may be readily and usefully employed in the therapeutic treatment and management of one or more types of cancer occuring in human hosts.

A further object of the present invention is to provide means and methods of creating useful pharmaceutical preparations for the treatment and management of cancer which preparations contain as their essential active ingredient a factor extracted from *Pancratium littorale* Jacq. and *Zephranthes grandiflora*, its synthetic replication, or a non-toxic pharmacologically active derivatives thereof.

These and still further objects, as shall hereinafter appear, are fulfilled by the present invention in a remarkably unexpected manner as will be readily discerned from the following detailed description of exemplary embodiments thereof.

BRIEF SUMMARY OF THE INVENTION

The present invention comprises the provision of new and useful chemotherapeutic agents which are extracted from the root of the Hawaiian (or African) *Pancratium littorale Jacq.* and *Zephranthes grandiflora* in the manner hereinafter described in detail, and which are thereafter formulated into useful pharmaceutical preparations having demonstratable and confirmed levels of anticancer activity when measured by the generally accepted protocols in use at the United States National Cancer Institute. The principal substance above referred to is herein denominated "Pancratistatin". The invention further contemplates the preparation of a synthetic counterpart and the non-toxic pharmacologically active derivative of pancratistatin and its pharmcologically active companion, 7-deoxynarciclasine.

One principal active ingredient of the present invention is a substance denominated pancratistatin having the structure:

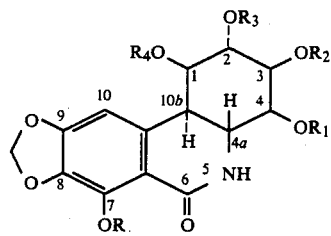

wherein $R=R_1=R_2=R_3=R_4=H$, the derivatives thereof wherein $R=R_1=R_2=R_3=R_4=COCH_3$ and wherein $R=CH_3$ and $R_1=R_2=R_3=R_4=H$.

A second active ingredient of the present invention is a substance denominated 7-deoxynarciclasine having the structure:

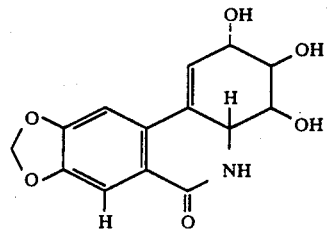

$R_1=R_2=R_3=H$,

DETAILED DESCRIPTION OF EMBODIMENTS

The bulb section (45 kg) of *P. littorale* was extracted with methylene chloride-methanol-water and pancratistatin was concentrated (separation was guided primarily by bioassay using the PS in vivo system) in a n-butanol extract of the aqueous phase. Purification of half of the crude product employing selective solubility properties and gel permeation chromatography (SEPHADEX ® LH-20) afforded 6.5 g (0.028% yield) of pancratistatin that separated from dimethylformanidemethanol-ether as a colorless solid: dp 320°–321°; EI mass spectrum m/e 325 (M+, $C_{14}H_{15}NO_8$) $[\alpha]^{32}$ +44° (c, 1.0, DMSO); $CH_3^{max}OH$ (log $\Sigma$) 229 (4.29), 239 (4.26) and 281 (4.0) nm; IR (KBr) $\nu_{max}$ 3500–3200, 1675, 1615, 1600, 1500, 1465, 1445, 1420, 1375, 1350, 1300, 1230, 1200, 1160, 1118, 1085, 1070, 1040, 1030, 930, 912, 880, 840, 720, 655, 640 and 610 cm$^{-1}$; and $^1H$ NMR (100 MHz, DMSO-d$_6$) $\delta$ 3.6–4.4 (6H), 4.72–5.70 (5H, removed by D$_2$O, 6.11 (2H, br. s), 6.56 (1H, s) and 13.15 (1H, removed by D$_2$O). Reaction of pancratistatin with acetic anhydridepyridine provided its pentaacetate (mp 162°–166°). Reaction of pancratistatin with diazomethane in methanol yielded the 7-monomethyl ether (mp 294°–298°). The same procedure provides pancratistatin from *Zephranthes grandiflora* although *P. littorale J.* is used herein as exemplarly.

The remarkable insolubility of pancratistatin in a variety of organic solvents, its high decomposition point, non-basic character, and infrared spectrum suggests a carbostyril or isocarbostyril system. The most plausible interpretation of the elemental analyses and spectral data for pancratistatin, the pentaacetate and the methyl ether point to a new phenanthridone. An x-ray crystal structure determination was utilized to make the stereochemical assignments and confirm the overall structure of pancratistatin as shown below.

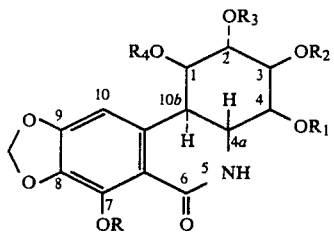

wherein: $R=R_1=R_2=R_3=R_4=H$.

A single crystal (0.125×0.25×0.37 mm) of pancratistatin monomethyl ether, recrystallized from 95% ethyl alcohol, was found to correspond with $C_{15}H_{17}NO_8 \cdot H_2O$, $f\omega$ 357.32; monoclinic B=99.78 (2)$_3$°, a=9.040(1), b=8.317(1) and c=10.187(2) Å; V=754.8 Å; F (000) =376; Po=1.565 g/cc, Z=2, and Pc=1.572 g/cc (25° C.; CuKα, λ=1.54184 Å).

Systematic extinctions (OkO absent if k=2n+1) and chirality were consistent with space group P2$_1$. The observed density of 1.56 g/cc indicated one molecular each of $C_{15}H_{17}NO_8$ and water per equivalent position (2 molecules of pancratistatin /cell). The cell parameters were obtained by a least-squares fit of the reciprocal lattice positions of 25 diffractometer measured reflections with 2-theta values in the range of 5°-35°. Intensities of all unique reflections with 2θ<75° were measured at 25° C. using a variable speed omega/2-theta scan technique on an Enraf-Nonius (Delft) CAD4 diffractometer employing graphite-monochromated CuKα radiation. The scan angle was calculated for each reflection as (0.90+0.15 tan θ)°. The detector aperature with a variable width of (4.0+0.5 tan 2) mm and a constant vertical height of 4 mm was positioned at a distance of 173 mm from the crystal. Maximum scan time for each reflection was 1 min. Two-thirds of this time was used to scan the peak and one-sixth in measuring ach of the two backgrounds. The intensities of three monitor reflections were also recorded ever 250 minutes and found to have varied by less than 0.5% during the entire data collection process. A total of 1647 unique reflections were retained for subsequent processing [I<1.0σ (I)]. All intensity data were corrected for anisotropic decay using the monitor intensities of the standards. The data were corrected for Lorentz-polarization and anomalous dispersion effects. Atomic scattering factor coefficients were taken from appropriate tables: D. T. Cromer and J. T. Waber, "International Tables for X-ray Crystallography," Vol. IV, The Kynoch Press, Birmingham, England, 1974, Table 2.2B; tables for anomalous dispersion coefficients, D. T. Cramer, ibid., Table 2.3.1. No extinction or absorption adjustments were made or deemed necessary ($\mu$=10.038 cm$^{-1}$).

Structural determination of pancratistatin monomethyl ether was achieved by direct methods using a multisolution weighted tangent formula approach, i.e., program MULTAN. All crystallographic calculations were accomplished with a PDP 11/23 computer using the Enraf-Nonius (Delft) Structure Determination Package (SDP-PLUS) software system developed by B. A. Frenz and Associates, Inc., College Station, Texas, 1982. Principal programs used were; START, PAINTER, REJECT, CHORT, data reduction programs; LSB, a full matrix last-squares refinement program; SEARCH, a connectivity peak search peak program; ORTEP-II the crystallographic illustration programs; MULTAN 11/82 "A System of Computer Programs for the Automatic Solution of Crystal Structures from X-ray Diffraction Data," a direct methods program by P. Main and colleagues, University of York, York, England. For a description of MULTAN see: Germain, G; Main, P.; Woolfson, M. M.; *Acta Crystallogr. Sect. B.*, 1970, 26, 274–285 and Woolfson, M. M. *Acta Crystallogr. Sect. B.*, 1977, 33, 219–225. After the correct assignment of co-ordinates for all non-hydrogen atoms, full matrix least-squares refinement the non-Poisson contribution weighting scheme was used in least-squares refinement, where $W=1/\sigma_{(F2)}=4\times F^2/(\propto_F 2)^2$ and $\propto_{(F^2)}=\sqrt{\propto I^2+(P\times F^2)^2}$, where P is an adjustment factor to downgrade intense reflections and W is the weight for the reflection. A value of 0.05 was used for P on all co-ordinates, scale factor and isotropic temperature factors resulted in a rapid reduction in the conventional unweighted crystallographic discrepancy index R($\Sigma|Fo-Fc|/\Sigma|Fo|$) to 0.1795 [for observed reflections, I>3σ (I)]. Subsequent difference electron density syntheses revealed all hydrogen atoms as well as the presence of one molecule of water, which appear to be hydrogen bonded (1.83 Å) to one of the hydroxy hydrogens at C-4. Finally, several additional cycles of full-matrix least-squares refinement of all variables (anisotropic nonhydrogen atoms and isotropic nonhydrogen atoms and isotropic hydrogens, with the thermal B values of the latter fixed at a nominal value of 5.0) caused convergence to R=0.405 (Rω=0.0438. Refinement was discontinued when parameter shifts became insignificant (maximum shift to error ratio was 0.84 with the majority in 0.1-0.2 range) and a final difference map revealed negligible electron densities (>0.22 e Å$^{-3}$). All bond lengths and angles agreed with expected values.

A calculation of the discrepancy indexes for the opposite enantiomorph of that depicted for the pancratistatin derivative (see Table I) when R=CH$_3$ and R$_1$=R$_2$=R$_3$=R$_4$=H, from the data (1632 observations and 301 variables) yielded values of R' =0.0425 and R'ω represents the absolute stereochemical configuration with >99.9% probability. Additional support for the absolute configurational assignment arises from a combination of biosynthetic and x-ray crystal structure studies of narciclasine, a 1-dehydrophenanthridone derivative of pancrastistatin.

In one practice of the present invention, the bulbs of *P. littorale* were extracted employing a methylene chloride-methanol procedure followed by the addition of water. The methylene chloride phase was partitioned using the solvent sequence 9:1→4:1→3:2 methanol-water with hexane→carbon tetrachloride→methylene chloride. The aqueous phase was extracted with n-butanol and pancratistatin was concentrated there rather than in the methylene chloride residue where lycorine would be expected.

The n-butanol fraction was further separated by gel permeation chromatography on SEPHADEX® LH-20 using methanol as eluent. Fraction collection was guided by thin layer chromatography using 3:1 chloroform-methanol. The two principal antineoplastic components corresponded to $R_f$ 0.37 and 0.46. Both proved to be very high melting, relatively insoluble, and nitrogen-containing non-basic solids reminiscent of carbostyrils or isocarbostyrils.

Purification of the $R_f$ 0.37 product by recrystallization from acetic acid-methanol afforded a lactam that readily gave a triacetate derivative. Spectral data indicated that this anticancer (PS, T/C 161 at 12.5 mg/kg, $ED_{50}$, 0.02 μg/ml) constituent was a 7-deoxy derivative of narciclasine. But physical constants reported for margetine, later renamed lycoricidine, indicated otherwise. For these reasons and because initial attempts to obtain an authentic sample of 7-deoxynarciclasine were unsuccessful, a complete structural determination was undertaken by x-ray crystallographic methods. The result was definite assignment of structure

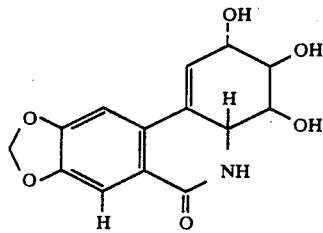

to the substance with $R_f$ 0.37. The absolute configuration of the triol was deduced from its presumed biosynthesis from vittatine. Later authentic samples of the triacetate

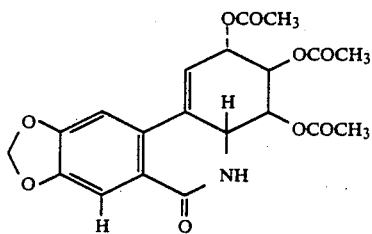

prepared from the natural and (±) synthetic products were obtained and infrared spectral comparison in potassium bromide with the substance with $R_f$ 0.37 P. littorale showed substantial differences, but when compared in a chloroform solution, the spectra were identical. On this basis the assignment of the above shown structure to 7-deoxynarciclasine is believed correct.

Recrystallization of the $R_f$ 0.46 anticancer (T/C 138→165 at 0.75→6.0 mg/kg dose levels and 206 at 12.5 mg/kg in the PS system with $ED_{50}$, 0.01 μg/ml) component from dimethylformamide-methanol-ether gave a pure specimen that displayed elemental analytical and spectral data in accord with the structure:

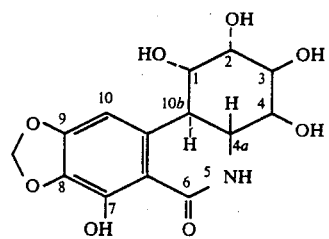

This new phenanathridone was denominated "pancratistatin" and its structural elucidation was accomplished by an x-ray crystal structure determination. The structure determined for pancratistatin was completely consistent with the corresponding spectral results.

To further aid in the understanding of the present invention, attention will now be directed to the procedures practiced in isolating pancratistatin and 7-deoxynnarciclasine from Hawaiian (African) *Pancraticm littorale Jacq.*

General Method. All solvents employed for chromatography were redistilled. Thin layer chromatography was performed on silica gel GHLF Uniplates (0.25 mm layer thickness) supplied by Analtech Inc., developing solvent chloroform:methanol (3:1) and visualized with ceric sulfate spray reagent. SEPHADEX® LH-20 (particle size 25–100 μ) was supplied by Sigma Chemical Co. A Gilson Model FC-200K fraction collector was used to collect fractions.

Melting points were determined on a Kofler-type hotstage apparatus and are uncorrected. Optical rotations were measured with a Perkin-Elmer Model 241 Automatic Polarimeter. Ultraviolet spectra were recorded on a Hewlett-Packard Model 8450A UV/VIS spectrophotometer and infrared spectra on Perkin Elmer Model 200 and Nicolet MX-1 FTIR spectrophotometers. $^1$H-and $^{13}$C-NMR spectra were recorded on Varian XL-100 and Bruker HXE-90 (22.63 MHz) spectrometers respectively, using tetramethylsilane as internal standard. Mass spectra were obtained on a varian MAT 312 spectrometer.

Extraction. The bulbs of the Hawaiian *P. littorale Jacq* were chopped and the chopped bulbs (45 kg) were extracted with methanol:methylene choloride (1:1, 320 liters) at ambient temperature for 20 days. The extract was then decanted and the methylene chloride phase separated by the addition of 20% by volume of water. The aqueous phase was adjusted by addition of further methanol and methylene chloride in the ratio, aqueous phase:methanol:methylene chloride (2:1:1) and the bulbs re-extracted for a further 20 days. Subsequent decantation and addition of 20% by volume of water separated the methylene chloride phase which was then combined with the first methylene chloride fraction and evaporated to give an inactive extract (812 g).

Solvent Partition. The aqueous phase from the above extraction was concentrated to approximately 16 liters and thereafter centrifuged to remove the insoluble material therefrom. The clear solution was then extracted with n-butanol (3×10 liters) and the butanol extract concentrated to give the butanol soluble fraction (705 g). An aliquot (355 g) was dissolved in methanol (1.5 liter) and acetone (3.5 liters) added. The insoluble material (105 g) was filtered and the filtrate evaporated to provide a residue (250 g).

Isolation of 7-Deoxynarciclasine and Pancratistatin. The residue obtained by the foregoing solvent partition was treated with methanol (1.5 liters) and thereafter filtered to produce a solid (2 g) shown to be pancratistatin. The filtrate was chromatographed on Sephadex LH-20 (2 kg; 105×10 cm) using methanol as eluent and monitoring the fractions by thin layer chromatography. Fractions containing the component $r_f$ 0.37 were combined, concentrated and filtered to provide 7-deoxynarciclasine (10 g) which crystallized from acetic acid-methanol as fine needles, mp 251°–252° [lit. 214.5°–2.15.5° (9); 230° (dec) (12)]; $[\alpha]^{33} + 157.3°$ (c 0.96, DMSO); ei ms: m/e 291 ($M^+$, $C_{14}H_{13}NO_6$); $\lambda_{max}^{CH3OH}$ (log Σ) 233(4.14), 248 (4.15) and 302 (3.75)nm; ir (KBr) $\nu_{max}$ 3450, 3250, 1672, 1632, 1620, 1602, 1505, 1473, 1415, 1400, 1340, 1320, 1270, 1250, 1080, 1045, 1015, 976, 940, 890, 860, 785, 700, 670 and 623 $cm^{-1}$; $^1H$ nmr (pyridine-$d_5$) δ, 4.81–4.92 (2H), 5.0–5.35 (2H), 6.05 (2H, d, J=a3 Hz), 6.72 (1H, br s), 7.33 (1H, s), 8.06 (1H, s), 8.57 (1H, s, removed by D exchange) and 7.0–8.6 (br hump, removed by $D_2O$) ppm; $^{132}C$ nmr (DMSO-$d_6$) δ163.12, 150,58, 147.72, 131.70, 130.01, 123.61, 121.95, 106.19, 103.24, 101.81, 72.56, 69.21 and 52.74 ppm (one carbon masked by DMSO: 42.77–36.72).

Anal calcd for $C_{14}H_{13}NO_6$: C, 57.73; H, 4.47; N, 4.81. Found: C, 57.79; H, 4.49; N, 4.79.

Further elution gave fractions containing mainly the component $R_f$ 0.46 which, on concentration and filtration, gave pancratistatin (4.5 g). Crystallization from dimethylformamide-methanol-ether gave a colorless solid, mp 320°–321° (dec); $[\alpha]_D^{32} + 44°$ (c 1.0, DMSO) eims m/e 325 ($M^+$, $C_{14}H_{15}NO_8$); $\lambda_{max}^{CH3OH}$ (log Σ) 209(sh), 219(sh), 233(4.32), 278(3.91) and 308 (br. sh)nm; ir (KBr) $\nu_{max}$3500–3200, 1675, 1615, 1600, 1500, 1465, 1445, 1420, 1375, 1350, 1300, 1230, 1200, 1160, 1118, 1085, 1070, 1040, 1030, 930, 912, 880, 840, 720, 655, 640 and 610 $cm^{-1}$; $^1H$ nmr (MDSO-$d_6$) δ 3.6–4.4 (6H), 4.72–5.70 (5H, removed by $D_2O$), 6.11 (2H, br. s), 6.56 (1H, s) and 13.15 (1H, removed by $D_2O$) ppm; $^{13}C$ nmr (DMSO-$d_6$) δ 169.49, 152.04, 145.38, 135.63, 131.70, 107.49, 101.70, 97.62, 73.28, 70.19, 69.99, 68.50 and 50.46 ppm (one carbon masked by DMSO:42.27–36.72).

Anal calcd for $C_{14}H_{15}NO_8$: C, 51.69; H, 4.61; N, 4.31. Found: C, 51.65; H, 4.55; N, 4.24.

Biologically active glycoside derivatives of pancratistatin and 7-deoxynarciclasine are made by coupling the principal with suitably protected sugars or other hydroxylated compounds using methods well known in the art [see Methods in Chemistry by R. L. Whistler and J. N. Bemiller (eds.), Academic Press, N.Y., 1972, Vol. 6, or The Carbohydrates: Chemistry and Biochemistry by W. Pigman, Academic Press, N.Y., 1981].

Derivatives of pancratistatin are used for the same purposes as pancratistatin.

Pancratistin and 7-deoxynarciclasine, as demonstrated, both have free hydroxyl groups available for derivatization. Thus, acyl esters of these compounds can also be prepared by methods well known to those skilled in the art. Acyl derivatives of the pancratistatins and 7-deoxynarciclasines can be used for the same biological purposes as the parent compounds.

Acids which can be used in the acylation of a pancratistatin include:

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncar-boxylic acids as given above which are substituted by one or more of halogen, nitro, hydroxy, keto, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid; α- and β-chloropropionic acid; α- and γ-bromobutyric acid; α- and δ-iodovaleric acid; mevalonic acid; 2- and 4-chlorocyclohexanecarboxylic acid; shikimic acid; 2-nitro-1-methyl-cyclobutanecarboxylic acid; 1, 2, 3, 4, 5, 6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,5-dibromo-2-methylcyclohexanecarboxylic acid; 4,5-dibromo-2-methylcyclohexanecarboxylic acid; 5, 6-dibromo-2-methylcyclohexanecarboxylic acid; 3-bromo-3-methylcyclohexanecarboxylic acid; 6-bromo-3-methylcyclohexanecarboxylic acid; 1,6-dibromo3-methylcyclohexanecarboxylic acid; 2-bromo-4-methylcyclocohexanecarboxylic acid; 1,2-dibromo-4-methylcyclohexanecarboxylic acid; 3-bromo-2, 2, 3-trimethylcyclopentanecarboxylic acid; 1-bromo-3,5-dimethylcyclohexanecarboxylic acid; homogentisic acid, o-, m-, and p-chlorobenzoic acid; anisic acid; salicylic acid; p-hydroxybenzoic acid; b-resorcylic acid; gallic acid; veratric acid; trimethoxybenzoic acid; trimethoxycinnamic acid; 4,4′-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicylic acid; mandelic acid; levulinic acid; pyruvic acid; glycine; alamine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid; aminoadipic acid; glutamine; asparagine; and the like.

7-Deoxynarciclasine Triacetate was prepared by reacting 7-Deoxynarciclasine (0.5 g) with acetic anhydride (2 ml) and pyridine (2 ml) at room temperature for 48 hours. Addition to ice water and filtration gave a product (0.5 g) which was chromatographed on silica gel-60 (Merck; 70-230 mesh). Elution with methylene chloride-methanol (99:1) gave the triacetate (0.35 g) which crystallized from methylene chloride-methanol as colorless needles, mp 244°-246° [lit. 201° (9,11), 233°-235° (12)]; $[\alpha]_D^{27}+219°$ (c 1.0, CHCl$_3$) [lit. $[\alpha]^{20}+195°$ (c 0.45, CHCl$_3$)(11)]; eims m/e 4.17 (M+C$_{20}$H$_{19}$NO$_9$); $\lambda_{max}^{CH3OH}$ (log $\Sigma$), 231(4.20), 251(4.21) and 305(3.93) nm; ir (KBr) $\nu_{max}$3392, 1760, 1748, 1733, 1663, 1640, 1615, 1500, 1485, 1470, 1400, 1373, 1364, 1263, 1245, 1225, 1076, 1040, 1015, 966, 940, 828 and 663 cm$^{-1}$; $^1$H nmr (CDCl$_3$) δ 2.12 (3H, s), 2.14 (3H, s), 2.19 (3H, s), 4.71 (1H, dd, J=9 and 2Hz), 5.32 (1H, dd, J=9 and 2Hz), 5.38 (1H, m), 5.55 (1H, m), 6.12 (1H, m), 6.12 (2H, s), 7.06 (1H, s), 7.24 (1H, br. s, removed by D$_2$O) and 7.59 (1H, s) ppm; $^{13}$C nmr (CDCl$_3$) δ 170.4, 169.79, 169.53, 164.52, 151.79, 149.25, 134.24, 130.43, 122.56, 117.12, 107.52, 103.43, 102.07, 71.23, 68.59, 68.30, 50.27, 21.02, 20.86 and 20.73 ppm.

Anal calcd for C$_{20}$H$_{19}$NO$_9$: C, 57.55; H, 4.55. Found: C, 57.37; H, 4.63.

The structure was solved by direct methods and atomic co-ordinates refined by full matrix least-squares programs provided in a structure solution package. Hydrogen atom co-ordinates were either calculated and/or located via difference maps and were included in the final refinement. The final standard crystallographic residuals (weighted and unweighted R factors) for the model, which contained anisotropic temperature factors for all heavy atoms and fixed (B=4.0) isotropic factors for all hydrogens, were 0.063 and 0.044, respectively. The maximum shift to error ratio in the last cycle of refinement was 0.55, with all bond distances and angles having nominal values.

Crystal data: C$_{20}$H$_{19}$NO$_9$, monoclinic, space group P2$_1$, with a=8.325(2), b=8.013(2), c=14.551(2)Å, V=946.4Å$^3$, Dm=1.45, Dc=1.46 g cm$^{-3}$ for Z=2. One quadrant of data on a crystal of dimensions ca. 0.10×0.15×0.75 mm was collected to a maximum of 2θ of 150° using the w/2θ scan technique and graphite monochromated Cu Kα radiation (λ 1.5418Å), and after Lorentz and polarization corrections, 1581 of the reflections with /F/≧3 σ (F) were used in the structure determination; absorbtion corrections were deemed unecessary (μ=9.5 cm$^{-1}$).

Pancratistatin Pentaacetate was prepared when pancratistatin (0.5 g) was treated in a similar manner to that described above for 7-deoxynarciclasine. The product (0.5 g) was chromatographed on Sephadex® LH-20 (100 g) using methanol-methylene chloride (3:2) as eluent to give the amorphous pentaacetate, mp 162°-166°; $[\alpha]^{29}+85°$ (c 1.0, CHCl$_3$); eims m/e 535 (M+,C$_{24}$H$_{25}$NO$_{13}$); $\lambda_{max}^{CH3OH}$ (log $\Sigma$) 227(4.31), 247(sh), 271(sh) and 299(3.75 nm); ir (KBr) $\nu_{max}$3370, 1760, 1680, 1635, 1510, 1490, 1375, 1340, 1295, 1250, 1220, 1180, 1080, 1045, 950, 930, 860, 815, 758 and 640 cm$^{-1}$; $^1$H nmr (90 MHz; CDCl$_3$) δ 2.06 (6H, s), 2.08 (3H, s), 2.17 (3H, s), 2.37 (3H, s), 3.43 (1H, dd, J=12.3 and 2.5 Hz), 4.26 (1H, dd, J=12.5 and 11.7 Hz), 5.14 (1H, dd, J=11.7 and 3.3 Hz), 5.22 (1H, dd, J=2.9 and 2.9 Hz), 5.45 (1H, m), 5.56 (1H, m), 5.76 (1H, br. s, removed by D$_2$O), 6.08 (2H, br. s) and 6.48 (1H, s) ppm; $^{13}$C nmr (CDCl$_3$) δ 170.08, 169.69, 169.07, 169.01, 168.29, 162.96, 152.60, 139.86, 134.53, 132.90, 116.20, 102.94, 101.84, 71.68, 67.69, 66.84, 66.42, 47.86, 40.00, 20.86 and 20.70 (last two signals 5 C) ppm.

Anal calcd for C$_{24}$H$_{25}$NO$_{13}$:C, 53.83; H, 4.67; N, 2.62. Found: C, 53.75; H, 4.68; N, 2.61.

Pancratistatin Methyl Ether was prepared by reacting pancratistatin (0.33 g) in methanol (100 ml) with excess diazomethane in ether. After stirring for 8 hours at room temperature an additional quantity of diazomethane was added and stirring continued 8 hours. Evaporation of the solvent gave a product (0.34 g) which was chromatographed on Sephadex® Sephadex® LH-20 using methanol as eluent to give the methyl ether (0.1 g). Crystallization from methanol gave colorless plates; mp 294°-298° (dec); $[\alpha]_D^{25}+289.9°$ (c 0.69, DMSO); ir (KBr) $\nu_{max}$3500, 3400, 3300, 1635, 1600, 1485, 1450, 1390, 1343, 1298, 1226, 1207, 1152, 1122, 1090, 1060, 1035, 967, 937, 920, 880, 840, 795, 724, 660 and 620 cm$^{-1}$; $^1$H nmr (DMSO-d$_6$) δ 3.58-4.44 (6H), 3.88 (3H, s), 4.70-5.50 (4H, removed by D$_2$O), 6.13 (2H, d, J=5 Hz), 6.74 (1H, s) and 6.92 (1H, removed by D$_2$O) ppm.

Anal calcd for C$_{15}$H$_{17}$NO$_8$: C, 53.10; H, 5.01; N, 4.13. Found: C, 53.44; H, 5.06; N, 4.08.

The administration of pancratistatin and its pharmacologically active physiologicaly compatible derivatives is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, broncholialy, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium sterate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such in syrups, elixirs and suspensions can be prepared wherein each teaspoonful of composition contains a predetermined amount of active ingredient for administation. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferrably P.F. water, a dry powder can be formulated when insufflation is the administration of choice.

For use as aerosols, the active ingredients can be packaged in a pressurized aerosol container together with a gaseous or liquified propellant, for example, dichlorodifluormethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE 1

Several dosage forms were prepared embodying the present invention. They are shown in the following examples in which the notation "active ingredient" signifies pancratistatin and 7-deoxynarciclasine, their synthetic counterparts and the non-toxic pharmaceutically active derivatives thereof.

COMPOSITION "A"

Hard-Gelatin Capsules

One thousand two-piece hard gelation capsules for oral use, each capsule containing 200 mg of an active ingredient are prepared from the following types and amounts of ingredients:

| | |
|---|---|
| Active ingredient, micronized | 200 gm |
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a active ingredient in 50, 250 and 500 mg amounts by substituting 50 gm, 250 gm and 500 gm of a active ingredient for the 200 gm used above.

COMPOSITION "B"

Soft Gelatin Capsules

One-piece soft gelatin capsules for oral use, each containing 200 mg of a active ingredient (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION "C"

Tablets

One thousand tablets, each containing 200 mg of a active ingredient are prepared from the following types and amounts of ingredients:

| Active ingredient micronized | 200 gm |
|---|---|
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing a active ingredient in 250 mg and 100 mg amounts by substituting 250 gm and 100 gm of a active ingredient for the 200 gm used above.

COMPOSITION "D"

Oral Suspension

One thousand ml of an aqueous suspension for oral use, containing in each teaspoonful (5 ml) dose, 50 mg of a active ingredient, is prepared from the following types and amounts of ingredients:

| Active ingredient micronized | 10 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml 300 mg of a active ingredient for treating a neoplastic disease, is prepared from the following types and amounts of ingredients:

| Active ingredient, micronized | 30 gm |
|---|---|
| Polysorbate 80 | 5 gm |
| Methylparaben | 2.5 gm |
| Propylparaben | 0.17 gm |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1M) three times a day.

COMPOSITION "F"

Suppository, Rectal and Vaginal

One thousand suppositories, each weighing 2.5 gm and containing 200 mg of a active ingredient are prepared from the following types and amounts of ingredients:

| Active ingredient, micronized | 15 gm |
|---|---|
| Propylene glycol | 150 gm |
| Polyethylene glycol #4000, q.s. | 2,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40°C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One thousand ml of a sterile aqueous suspension for intranasal instillation, containing in each ml 200 mg of a active ingredient, is prepared from the following types and amounts of ingredients:

| Active ingredient, micronized | 15 gm |
|---|---|
| Polysorbate 80 | 5 gm |
| Methylparaben | 2.5 gm |
| Propylparaben | 0.17 gm |
| Deionized water, q.s. 1000 ml. | |

All the ingredients, except the active ingredient, are dissolved in the water and the solution sterilized by filtration. To the sterile solution is added the sterilized acitve ingredient, finely divided by means of an air micronizer, and the final suspension is aseptically filed into sterile containers.

The composition so prepared is useful for treating a neoplastic disease, by intranasal instillation of 0.2 to 0.5 ml given one to four times per day.

An active ingredient can also be present, as shown in Examples 12-14 in the undiluted pure form for use locally about the cutis, intranasally, pharyngolaryngeally, bronchially, broncholially or orally.

COMPOSITION "H"

Power

Five grams of a active ingredient in bulk form is finely divided by means of an air micronizer. The micronized power is placed in a shaker-type container.

The foregoing composition is useful for treating a neoplastic disease, at localized sites by applying a powder one to four times per day.

COMPOSITION "I"

Oral Powder

One hundred grams of a active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of a active ingredient in bulk form is finely divided by means of an air micronizer.

The foregoing composition is useful for treating a neoplastic disease, by the inhalation of 300 mg one to four times per day.

COMPOSITION "K"

Hard Gelatin Capsules

One hundred two-piece hard gelatin capsules for oral use, each capsule containing 200 mg of a active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 50, 250 and 500 mg amounts by substituting 50 gm, 250 gm and 500 of the active ingredient for the 200 gm used above.

EXAMPLE 2

Unit dosage forms of pancratistatin prepared according to selected compositions described in Example 1 were screened utilizing Protocol 1,200 described in *Cancer Chemotherapy Reports*, part 3, Vol. 3, No. 2, Sept. 1972, pp 9 et seq for lymphocytic leukemia P388. Pancratistatin provided a 38-106% life extension at 0.75-12.5 mg/Kg host body weight against the murine P388 lymphocytic leukemia. Pancratistatin also markedly inhibited growth of the P388 in vitro cell line ($ED_{50}$, 0.001 μg/ml).

EXAMPLE 3

Unit dosage forms of 7-deoxynarciclasine were prepared according to Example 1 and were screened using accepted protocols of the National Cancer Institute. The preparation obtained up to 61% life extension at 12 mg per kg host body weight against murine P388 lympocytic leukemia and an ED 50 of 0.02 micrograms per ml against the P388 cell line.

EXAMPLE 4

A unit dosage form of pancratistatin, prepared according to Example 1, was challenged with M5074 murine ovary sarcoma and obtained a 53% to 84% life extension at 0.38 to 3.0 mg active reagent/Kg host body weight using the National Cancer Institute accepted protocol for life extension.

EXAMPLE 5

A unit dosage form of pancratistatin, prepared according to Example 1, was subjected to the National Cancer Institute accepted protocol for cure rate against its M5074 murine ovary sarcoma and obtained a 50% cure rate at 6 mg/Kg host body weight.

From the foregoing it becomes readily apparent that a new an useful antineoplastic factor and new and useful antineoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention which is limited only by the scope of the claims appended hereto.

Accoridngly, what is claimed is:

1. An antineoplastic substance denominated pancratistatin.

2. An antineoplastic substance having the structural formula:

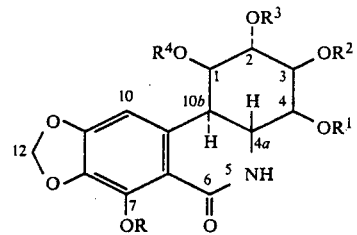

wherein:
R=H, $CH_3$ or COX;
$R_1$=H or COX;
$R_2$=H or COX;
$R_3$=H or COX;
$R_4$=H or COX; and
$X^4$=a radical of alkyl (C—1—20); alkenyl (C=1—20), aryl (C=9—12), or heterocyclic selected from the group consisting of thiazoyl, thiophenoyl, pyridoyl, pyrimidoyl and furoyl.

3. An antineoplastic substance according to claim 2 wherein R=H and $R_1=R_2=R_3=R_4$=H.

4. An antineoplastic pharmaceutical preparation containing as its principal active ingredients an effective amount of natural or synthetic substances or pharmaceutically active derivatives thereof a first substance having the structure

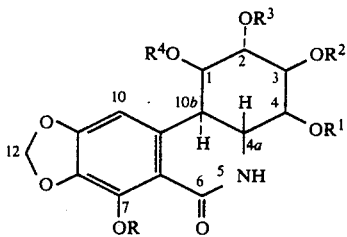

wherein:
R=H, CH₃ or COX;
R₁=H or COX;
R₂=H or COX;
R₃=H or COX;
R₄=H or COX; and
X⁴=a radical of alkyl (C—1—20), alkenyl (C=1—20), aryl (C=9—12), or heterocyclic selected from the group consisting of thiazoyl, thiophenoyl, pyridoyl, pyrimidoyl and furoyl;
and a second substance having the structure "B"

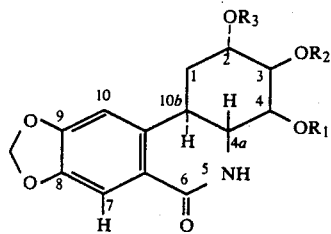

wherein:
R₁=H, COOH₃ or COX;
R₂=H, COCH₃ or COX;
R₃=H, COCH₃ or COX; and
X³=a radical of alkyl (C—1—20); alkenyl (C=1—20), aryl (C=9—12), or heterocyclic selected from the group consisting of thiazoyl, thiophenoyl, pyridoyl, pyrimidoyl and furoyl.

5. An antineoplastic pharmaceutical preparation according to claim 4 in which said substance has the "A" structure wherein: R=R₁=R₂=R₃=H.

6. An antineoplastic preparation according to claim 4 in which said second substance has the "B" structure wherein: R=H and R₁=R₂=R₃=H.

7. An antineoplastic pharmaceutical preparation according to claim 5 having the "B" structure wherein: R=H and R₁=R₂=R₃=H.

8. A substance according to claim 2 in which said COX has the structure:

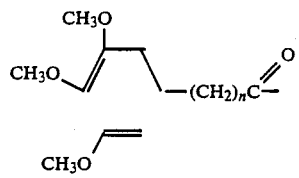

wherein: n=0–2.

9. A substance according to claim 2 in which said COX has the structure:

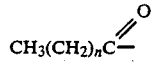

wherein: n=0 to 19.

10. A substance according to claim 2 in which said COX has the structure:

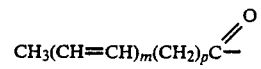

wherein:
m=0–3
p=0–16

* * * * *